US009044183B1

(12) United States Patent
Karam

(10) Patent No.: US 9,044,183 B1
(45) Date of Patent: *Jun. 2, 2015

(54) INTRA-VIDEO RATINGS

(75) Inventor: Joseph F. Karam, Mountain View, CA (US)

(73) Assignee: Google Inc., Mountain View, CA (US)

( * ) Notice: Subject to any disclaimer, the term of this patent is extended or adjusted under 35 U.S.C. 154(b) by 683 days.

This patent is subject to a terminal disclaimer.

(21) Appl. No.: 13/363,358

(22) Filed: Jan. 31, 2012

Related U.S. Application Data

(63) Continuation of application No. 12/414,553, filed on Mar. 30, 2009, now Pat. No. 8,132,200.

(51) Int. Cl.
*H04N 7/173* (2011.01)
*H04H 60/32* (2008.01)
*H04H 60/33* (2008.01)
*A61B 5/16* (2006.01)
*A61B 5/0205* (2006.01)
*A61B 5/024* (2006.01)

(52) U.S. Cl.
CPC .............. *A61B 5/165* (2013.01); *A61B 5/02055* (2013.01); *A61B 5/02405* (2013.01)

(58) Field of Classification Search
USPC ....................................... 725/9, 13, 14, 16, 24
See application file for complete search history.

(56) References Cited

U.S. PATENT DOCUMENTS

| | | |
|---|---|---|
| 5,339,393 A | 8/1994 | Duffy et al. |
| 5,388,197 A | 2/1995 | Rayner |
| 5,414,806 A | 5/1995 | Richards |
| 5,530,861 A | 6/1996 | Diamant et al. |
| 5,600,775 A | 2/1997 | King et al. |
| 5,664,216 A | 9/1997 | Blumenau |
| 5,708,845 A | 1/1998 | Wistendahl et al. |
| 5,732,184 A | 3/1998 | Chao et al. |
| 5,996,121 A | 12/1999 | Harris |
| 6,006,241 A | 12/1999 | Purnaveja et al. |
| 6,415,438 B1 | 7/2002 | Blackketter et al. |

(Continued)

FOREIGN PATENT DOCUMENTS

| | | |
|---|---|---|
| JP | 2004-080769 | 3/2004 |
| JP | 2006-157689 | 6/2006 |

(Continued)

OTHER PUBLICATIONS

Office Action for Canadian Patent Application No. CA-2,672,757, Mar. 21, 2013, 5 Pages.

(Continued)

*Primary Examiner* — Nasser Goodarzi
*Assistant Examiner* — Fred Peng
(74) *Attorney, Agent, or Firm* — Fenwick & West LLP

(57) ABSTRACT

A system and method is provided for receiving and displaying voting data with respect to online hosted videos. Viewers vote on portions within various videos stored in an online video hosting website. Voting data can represent different types of votes, such as unipolar, bipolar, or categorical. The prior voting data, including that submitted by other viewers, can be displayed in a number of ways, such as gradations of color, or charts such as bar graphs. The voting data may be associated with demographic categories, such as a voter's age, sex, or political affiliation. Further, a video may be selectively played to display portions of most interest to given demographic categories, as indicated by voting patterns of those categories.

22 Claims, 9 Drawing Sheets

(56) References Cited

U.S. PATENT DOCUMENTS

| | | | |
|---|---|---|---|
| 6,570,587 B1 | 5/2003 | Efrat et al. | |
| 6,774,908 B2 | 8/2004 | Bates et al. | |
| 6,956,593 B1 | 10/2005 | Gupta et al. | |
| 7,131,059 B2 | 10/2006 | Obrador | |
| 7,383,497 B2 | 6/2008 | Glenner et al. | |
| 7,418,656 B1 | 8/2008 | Petersen | |
| 7,559,017 B2 | 7/2009 | Datar et al. | |
| 7,636,883 B2 | 12/2009 | Albornoz et al. | |
| 7,724,277 B2 | 5/2010 | Shingu et al. | |
| 8,181,201 B2* | 5/2012 | Goldenberg et al. | 725/46 |
| 8,202,167 B2 | 6/2012 | Ackley et al. | |
| 8,209,223 B2 | 6/2012 | Fink et al. | |
| 8,280,827 B2 | 10/2012 | Muller et al. | |
| 8,392,834 B2 | 3/2013 | Obrador | |
| 8,839,327 B2* | 9/2014 | Amento et al. | 725/110 |
| 2001/0023436 A1 | 9/2001 | Srinivasan et al. | |
| 2002/0069218 A1 | 6/2002 | Sull et al. | |
| 2002/0078092 A1 | 6/2002 | Kim et al. | |
| 2002/0188630 A1 | 12/2002 | Davis et al. | |
| 2003/0002851 A1 | 1/2003 | Hsiao et al. | |
| 2003/0018668 A1 | 1/2003 | Britton et al. | |
| 2003/0039469 A1 | 2/2003 | Kim | |
| 2003/0093790 A1 | 5/2003 | Logan et al. | |
| 2003/0112276 A1 | 6/2003 | Lau et al. | |
| 2003/0196164 A1 | 10/2003 | Gupta et al. | |
| 2004/0021685 A1 | 2/2004 | Denoue et al. | |
| 2004/0168118 A1 | 8/2004 | Wong et al. | |
| 2004/0172593 A1 | 9/2004 | Wong et al. | |
| 2005/0160113 A1 | 7/2005 | Sipusic et al. | |
| 2005/0203876 A1 | 9/2005 | Cragun et al. | |
| 2005/0275716 A1 | 12/2005 | Shingu et al. | |
| 2005/0289469 A1 | 12/2005 | Chandler et al. | |
| 2006/0041564 A1 | 2/2006 | Jain et al. | |
| 2006/0053365 A1 | 3/2006 | Hollander et al. | |
| 2006/0064733 A1 | 3/2006 | Norton et al. | |
| 2006/0087987 A1 | 4/2006 | Witt et al. | |
| 2006/0101328 A1 | 5/2006 | Albornoz et al. | |
| 2006/0286536 A1 | 12/2006 | Mohler et al. | |
| 2006/0294134 A1 | 12/2006 | Berkhim et al. | |
| 2007/0038610 A1 | 2/2007 | Omoigui | |
| 2007/0099684 A1 | 5/2007 | Butterworth | |
| 2007/0121144 A1 | 5/2007 | Kato | |
| 2007/0250901 A1 | 10/2007 | McIntire et al. | |
| 2007/0256016 A1 | 11/2007 | Bedingfield | |
| 2007/0266304 A1 | 11/2007 | Fletcher et al. | |
| 2008/0005064 A1 | 1/2008 | Sarukkai | |
| 2008/0086742 A1* | 4/2008 | Aldrey et al. | 725/24 |
| 2008/0168070 A1 | 7/2008 | Naphade et al. | |
| 2008/0168073 A1 | 7/2008 | Siegel et al. | |
| 2009/0150947 A1 | 6/2009 | Soderstrom | |
| 2009/0172745 A1 | 7/2009 | Horozov et al. | |

FOREIGN PATENT DOCUMENTS

| | | |
|---|---|---|
| JP | 2007-151057 | 6/2007 |
| JP | 2007-274090 | 10/2007 |
| JP | 2007/529822 | 10/2007 |
| JP | 2007-310833 | 11/2007 |
| WO | WO 2007/082169 A2 | 7/2007 |

OTHER PUBLICATIONS

Office Action for Japanese Patent Application No. P2010-546967, Apr. 23, 2013, 5 Pages.
Chinese First Office Action, Chinese Application No. 200910206036.4, Sep. 18, 2012, 19 pages.
European Extended Search Report, European Application No. 09709327.2, Sep. 21, 2012, 7 pages.
Supplementary European Search Report for European Patent Application No. EP 07865849.9, May 18, 2012, 7 Pages.
First Office Action for Chinese Patent Application No. CN 200980108230.7, Feb. 28, 2012, 11 Pages.
Rejection Decision for Chinese Patent Application No. CN 200780050525.4, Jan. 18, 2012, 23 Pages.
Caspi, Y., et al., "Sharing Video Annotations," International Conference on Image Processing, 2004, pp. 2227-2230.
Gordon, A., "Using Annotated Video as an Information Retrieval Interface," IUI ACM, 2000, pp. 133-140.
Office Action for Canadian Patent Application No. CA 2,726,777, Nov. 26, 2012, 3 Pages.
Extended European Search Report for European Patent Application No. EP 09711777.4, Dec. 12, 2012, 8 Pages.
Miyamori, H., et al., "Generation of Views of TV Content Using TV Viewers' Perspectives Expressed in Live Chats on the Web," Proceedings of the 13th Annual ACM International Conference on Multimedia, Nov. 6, 2005, pp. 853-861.
Notification of Reexamination Board Opinion for Chinese Patent Application No. 200780050525.4, Jun. 14, 2013, 11 Pages.
Schroeter, R., et al., "Vannotea—A Collaborative Video Indexing, Annotation and Discussion System for Broadband Networks," Knowledge Capture, 2006, pp. 1-8.
First Examination Report for Indian Patent Application No. 1191/MUMNP/2009, Mar. 18, 2014, 2 Pages.
Chinese Second Office Action, Chinese Application No. 200980108230.7, Aug. 13, 2012, 11 pages.
Notification of Second Board Opinion for Chinese Patent Application No. CN 200780050525.4, Dec. 26, 2013, 5 Pages.
Communication Pursuant to Article 94(3) EPC for European Patent Application No. EP 09709327.2, Jan. 10, 2014, 6 Pages.
Europe Summons Notice, EP Application No. Application No. 09709327.2, Sep. 9, 2014, 9 pages.
China Second Office Action, Chinese Application No. 200780050525.4, Sep. 16, 2014, 21 pages.
Korean Office Action, Korean Application No. 10-2010-7020965, Feb. 26, 2015, 12 pages (with concise explanation of relevance).

* cited by examiner

INTRA-VIDEO RATINGS

RELATED APPLICATIONS

This application is a continuation of U.S. patent application Ser. No. 12/414,553, filed on Mar. 30, 2009, which application is incorporated herein by reference.

TECHNICAL FIELD

The present invention generally relates to the management and display of votes associated with video.

BACKGROUND

The proliferation of video sharing through websites provides numerous opportunities for users to collaborate and experience videos in online communities. Video hosting websites allow users to upload, view, and rate videos. Users browsing a video hosting website can locate videos of interest by, for example, searching for videos, browsing directories, or sorting by ratings.

User rating of videos provides a way to complement video with useful information. However, because conventional systems allow user rating only of a video as a whole, it cannot be determined which segments of the video the users found particularly interesting. This is especially problematic in light of increasingly large video length maximums allowed by video sharing websites, which leads to the presence of long videos, only a small portion of which may be interesting to most users. In addition, there is no way to navigate videos to find the most popular segments of a video. Although a user may wish to view only the most popular segments of the video, the user is obliged to view the entire video because the most popular parts of the video have not been determined. This results in considerable waste of time and user frustration.

SUMMARY

The present invention includes systems and methods for receiving and displaying voting data for a plurality of viewers of online videos hosted in a video hosting service. In one embodiment, a video hosted on the service is provided to the viewers via their client devices. The viewers vote as to their opinion on segments of the videos as they are being displayed on the viewers' devices. For example, the viewers can vote on whether they agree or disagree with the content of each segment. Each voter thus provides a series of votes corresponding to the segments of the video. For example, if a 1 minute video has 10 six-second segments, each viewer may cast 10 votes; or the video may have 60 one-second segments in which case a viewer can cast sixty votes. Alternatively, segments in a video can have variable length, with some segments being longer or shorter than other segments.

Each vote has a value that is selected from a unipolar or multipolar set of potential values, such as bipolar (e.g., agree/disagree, favorable/unfavorable, funny/not funny), or categorical votes.

The votes are transmitted from the client devices and received by the video hosting service. For each segment of the video, the votes can be aggregated according to their vote values; this aggregation is preferably, though not necessarily, done while the video is being provided to the client devices. For example, where the viewers can provide either a favorable or unfavorable vote, the number of favorable and unfavorable votes for each segment can be determined. The aggregated information reveals the aggregate opinion or judgment of the viewers for each segment of the video, and thus how that opinion may have changed throughout the video.

The video hosting service transmits information about the aggregated votes for the previously displayed segments, such as a graphical or numerical representation (e.g., totals for each vote value), to the viewer's client device, where it can be displayed in a number of ways, such as gradations of color, or charts such as bar graphs. The display of the aggregated information is preferably done while the video is still playing. Thus, as the viewer is watching the video and voting, she also sees the aggregated voting information for segments of the video that have already been shown. In one embodiment, the aggregated information is displayed on a timeline representation.

The voting data may be associated with demographic categories, such as a viewer's age, sex, or political affiliation; the votes can be aggregated according those demographic categories, and information about the demographic aggregation can be provided to the client devices for display thereon. Further, a video may be selectively played to display segments of most interest to given demographic categories, as indicated by voting patterns of those categories.

In one embodiment, a computer-implemented method of associating a series of votes with a video, wherein the video has a plurality of segments, comprises transmitting the video for display to a client device of a viewer, whereby the client device plays back the video for viewing by the viewer, and receiving a first series of votes from the viewer while the video is being played back on the client device, each vote associated with one of the segments of the video and having a vote value, the vote value selected by the viewer from a multipolar set of potential values. The method further comprises storing the first series of votes in a storage medium in association with information identifying the video.

The features and advantages described in this summary and the following detailed description are not all-inclusive. Many additional features and advantages will be apparent to one of ordinary skill in the art in view of the drawings, specification, and claims presented herein.

The figures depict various embodiments of the present invention for purposes of illustration only. One skilled in the art will readily recognize from the following discussion that alternative embodiments of the structures and methods illustrated herein may be employed without departing from the principles of the invention described herein.

DESCRIPTION OF EMBODIMENTS

Figure 1:
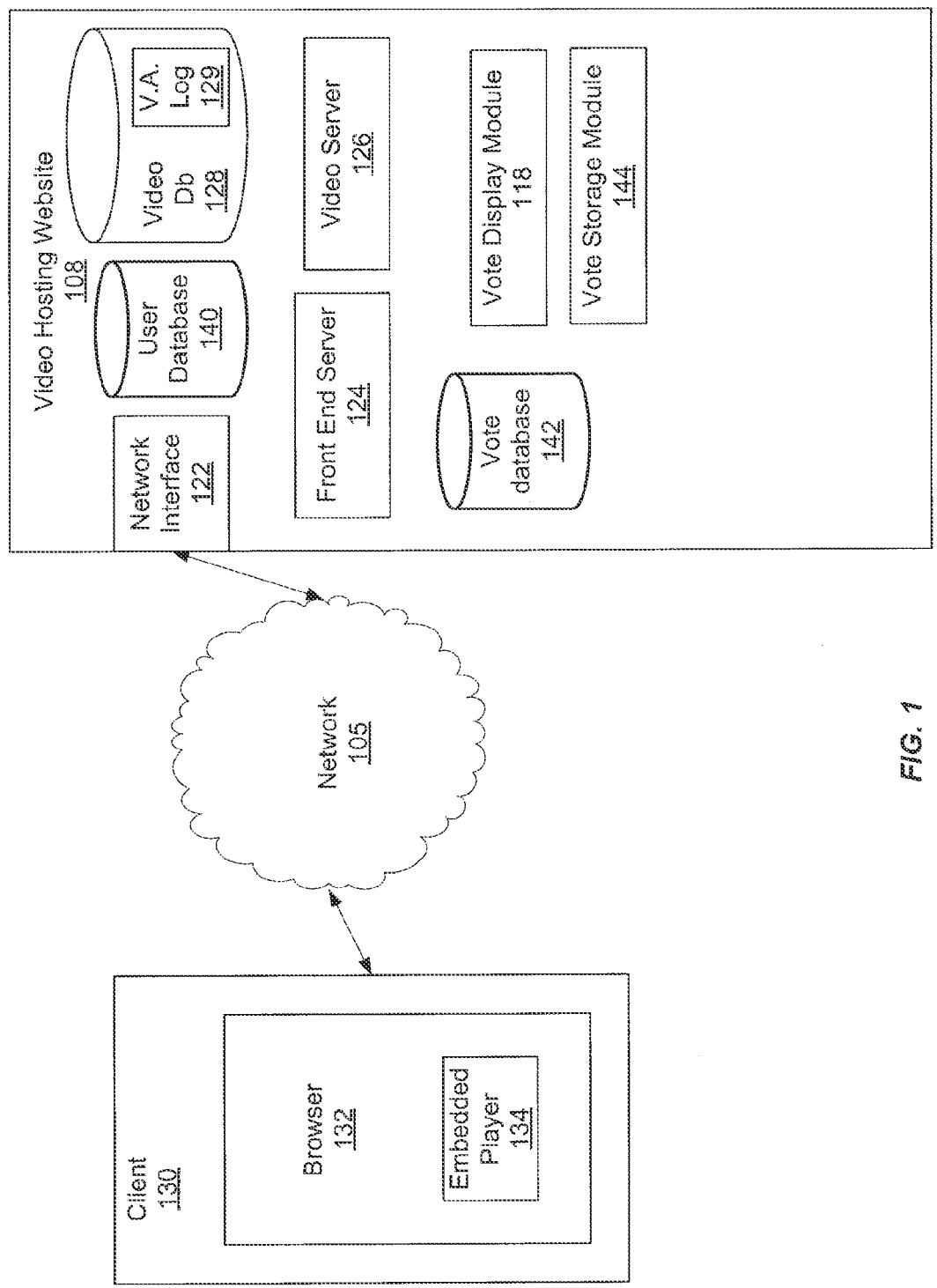
FIG. 1 is a block diagram of a system architecture for receiving and displaying voting data associated with online hosted videos in accordance with one embodiment of the present invention.

FIG. 1 is a block diagram of a system architecture in accordance with one embodiment. As illustrated in FIG. 1, a video hosting website 108 includes a front end server 124, a video server 126, a network interface 122, a video database 128, a video access log 129, a user database 140, a vote database 142, a vote display module 118, and a vote storage module 144. Other conventional features, such as firewalls, load balancers, application servers, failover servers, site management tools, and so forth are not shown so as to more clearly illustrate the features of the system. Examples of a suitable website 108 for implementation of the system include the YouTube™ and Google Video™ websites; other video hosting sites are known as well, and can be adapted to operate according the teaching disclosed herein. It will be understood that the term "website" represents any system and method of providing content and is not intended to be limited to systems that support content provided via the Internet or the HTTP protocol. The various servers are conventionally implemented, whether as a single piece of software or hardware or as multiple pieces of software or hardware and can couple to the network 105 via the network interface 122. In general, functions described in one embodiment as being performed on the server side can also be performed on the client side in other embodiments if appropriate.

A client 130 executes a browser 132, and connects to the front end server 124 via a network 105, which is typically the Internet, but may also be any network, including but not limited to a LAN, a MAN, a WAN, a mobile, wired or wireless network, a private network, or a virtual private network. While only a single client 130 and browser 132 are shown, it is understood that very large numbers (e.g., millions) of clients are supported and can be in communication with the website 108 at any time. The client 130 may include a variety of different computing devices. Examples of client devices 130 are personal computers, digital assistants, personal digital assistants, cellular phones, mobile phones, smart phones or laptop computers. As will be obvious to one of ordinary skill in the art, the present invention is not limited to the devices listed above.

In some embodiments, the browser 132 includes an embedded video player 134 such as, for example, the Flash™ player from Adobe Systems, Inc. or any other player adapted for the video file formats used in the video hosting website 108. A user can access a video from the video hosting website 108 by browsing a catalog of videos, conducting searches on keywords, reviewing play lists from other users or the system administrator (e.g., collections of videos forming channels), or viewing videos associated with particular user group (e.g., communities).

Video server 126 receives uploaded media content, such as videos, from content providers and allows content to be viewed by the client 130. Content providers may be users, commercial enterprises, and the like. Content may be uploaded to video server 126 via the Internet from a personal computer, through a cellular network from a telephone or PDA, or by other means for transferring data over network 105 known to those of ordinary skill in the art. Content may be downloaded from video server 126 in a similar manner; in one embodiment media content is provided as a file download to a client 130; in an alternative embodiment, media content is streamed to client 130. The means by which media content is received by video server 126 need not match the means by which it is delivered to client 130. For example, a content provider may upload a video via a browser on a personal computer, whereas client 130 may view that video as a stream sent to a PDA. Note also that video server 126 may itself serve as the content provider.

Users of clients 130 can also search for videos based on keywords, tags or other metadata. These requests are received as queries by the front end server 124 and provided to the video server 126, which is responsible for searching the video database 128 for videos that satisfy the user queries. The video server 126 supports searching on any fielded data for a video, including its title, description, tags, author, category and so forth. User can also browse for videos of interest via categories, channels, lists or other means.

Users of the clients 130 and browser 132 can upload content to the video hosting website 108 via network 105. The uploaded content can include, for example, video, audio or a combination of video and audio. The uploaded content is processed and stored in the video database 128. This processing can include format conversion (transcoding), compression, metadata tagging, and other data processing. An uploaded content file is associated with the uploading user, and so the user's account record is updated in the user database 140 as needed. Each uploaded video is assigned a video identifier when it is processed.

For purposes of convenience and the description of one embodiment, the uploaded content will be referred to as "videos", "video files", or "video items", but no limitation on the types of content that can be uploaded are intended by this terminology.

The video database 128 is used to store the received videos. The video database 128 stores video content and associated metadata, provided by their respective content owners. The video files have metadata associated with each file such as a video ID, artist, video title, label, genre, and time length. The video file data may be viewed as comprising a number of video segments with which votes may be associated. For example, in one embodiment segments are coherent portions of the video, e.g. a 5-second clip in a video of a debate of a candidate from a particular viewing angle, as determined by a video segmentation algorithm. The segmentation could be determined based on characteristics of the video data itself, such as scene changes, or on voting data, such as that created by clustering votes nearby in time to find the boundaries of the various segments. Since a segment's start and end points can be determined based on, e.g., scene changes, the various segments can have variable lengths with respect to each other. In another embodiment, a video can be segmented into a set of fixed-length segments, such as 1-second segments, or 10-second segments, or individual frames.

Information about the votes received is stored in the user database 140. The user database 140 is responsible for maintaining a record of all users viewing videos on the website. Each individual user is assigned a user ID. The user ID can be based on any identifying information, such as the user's IP address, user name, or the like. The user database may also contain information about the reputation of the user in the video context, as well as through other applications, such as the use of email or text messaging.

A video access log 129 within video database 128 stores each instance of video access. Each entry in the access log 129 identifies a video being accessed, a time of access, an IP address of the user, a user ID if available, cookies, search queries, data identifying the type of interaction with the video, and the time of every interaction with the video. Interaction types can include any user interactions in the user interface of the website 108, such as playing, pausing, rewinding, forwarding and submitting votes or ratings for a video.

A vote database 142 stores votes entered by users for the various videos of the video database 128. Votes may be represented in the vote database 142 as a vote value associated with a segment or segments of a video, such as a single frame or segment. Vote values may comprise various types of data in different embodiments, representing the different types of votes and what data is tracked. In one embodiment, a vote value type is "unipolar," merely representing a single concept, such as interest or favorability, and thus need have no associated value. In other embodiments, a vote value type is "multipolar," i.e. having a plurality of potential values. One type of multipolar vote is "bipolar," representing two distinct possibilities, such as "like"/"dislike", "favorable"/"unfavorable", "positive"/"negative", "interesting"/"not interesting", and the like. Another type of multipolar vote is a "categorical" vote, in which, a vote can take on one of a number of values for a given category; as one example, a vote describing the user's subjective emotional reaction to the video could have possible values representing reactions such as "clever", "boring", "interesting", "inspiring", "frightening" and the like. In general, a multipolar vote may represent data from any one of a number of different domains, such as a set of integers, or a continuous range of real numbers. The values may be orderable, such as votes representing levels of favorability, such as "poor", "OK", "good", and "great", or they may not be orderable, such as categories representing different unrelated emotions such as "clever", "inspiring", "frightening", etc.

Votes also have an associated temporal indicator indicating when the vote was submitted, which allows the derivation of statistics on patterns of voting over time within a given video. The temporal indicator may take different forms in different embodiments. For example, in one embodiment the temporal indicator indicates a particular time at which the vote was specified, e.g. a number of seconds into the video. In this case, the video hosting website 108 can map this time to a particular segment, through either a function or a stored map that identifies the times at which the segment boundaries of the video occur.

In another embodiment, the temporal indicator instead is an index of a segment; for example, for an embodiment having fixed length segments of 10 seconds, votes specified 45 seconds and 108 seconds into the video could be given zero-based indices of 5 and 11, indicating that they are in the 5th and 11th of the 10-second segments, respectively. In one embodiment, the calculation of the index is performed by the client at the time the vote is specified, e.g. by performing integer division of the second offset into the video by the fixed number of seconds per segment.

The temporal indicators can be specified as absolute values relative to the start of the video as described above, or can be relative offsets from the previous indicator; with the first temporal indicator being an offset from the beginning of the video, either in time (e.g., milliseconds) or frames, and then each following temporal indicator being the amount of time or number of frames from the prior indicator.

Regardless of which type of temporal identifier is provided to the video hosting website 108, the server can use it to determine a particular segment with which the vote is associated.

Votes may also have associated data such as demographic categories associated with the user who submitted the vote, e.g., gender, age group, political party affiliation, or other categories of interest. This information allows for even finer grained analysis of voting patterns for a given video.

A vote storage module 144 stores vote data provided by the client within the vote database 142. The vote storage module 144 can additionally store vote-related information, such as a vote timestamp, vote totals for a given segment of a video, and the like.

Figure 2:
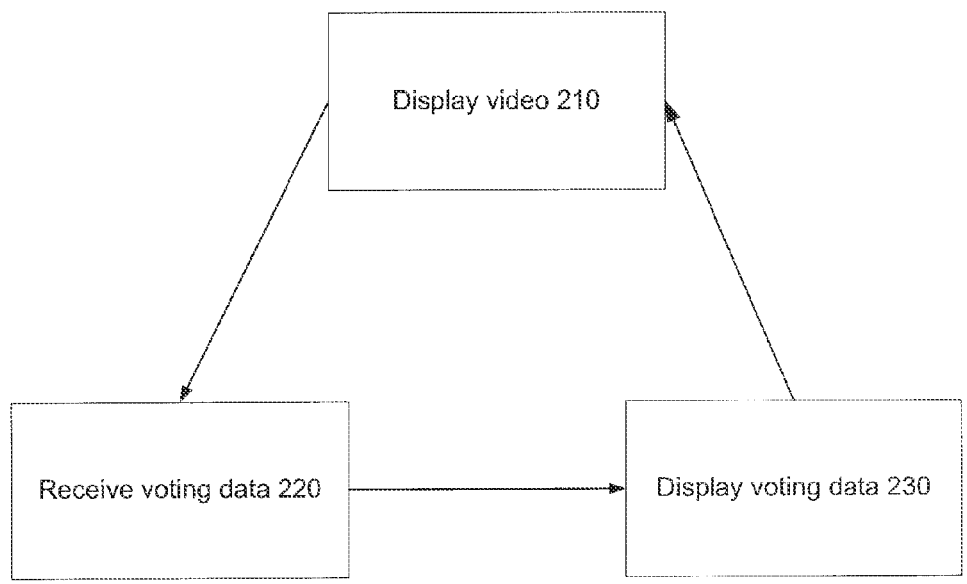
FIG. 2 illustrates steps performed by a client related to voting on videos, according to one embodiment.

FIG. 2 illustrates steps performed by the client 130 of FIG. 1. At one point, the client 130 displays 210 a video. While the video is being displayed, the client 130 receives 220 voting data from the user as inputs to the client 130. Client 130 also displays 230 the received voting data in association with the video. Note that these steps need not be performed in a linear sequence. For example, prior votes for a video have typically been received 220 by the time that the video is displayed 210.

Further, any prior voting data may be displayed 230 before the receipt of additional voting data at step 220. These steps are now discussed in further detail in conjunction with FIGS. 3A-3G, which illustrate different aspects of user interfaces for receiving and displaying voting data according to various embodiments.

Figure 3A:
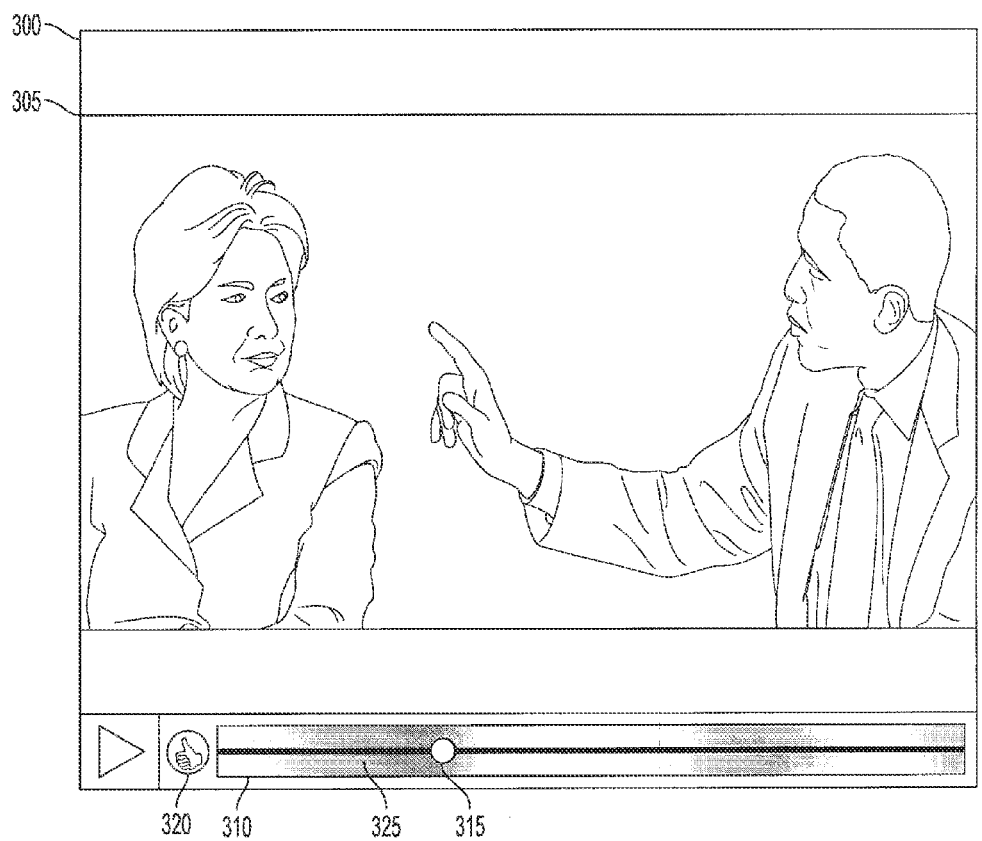
FIGS. 3A-3G illustrate user interfaces for use with voting on videos, according to different embodiments.
Figure 3B:
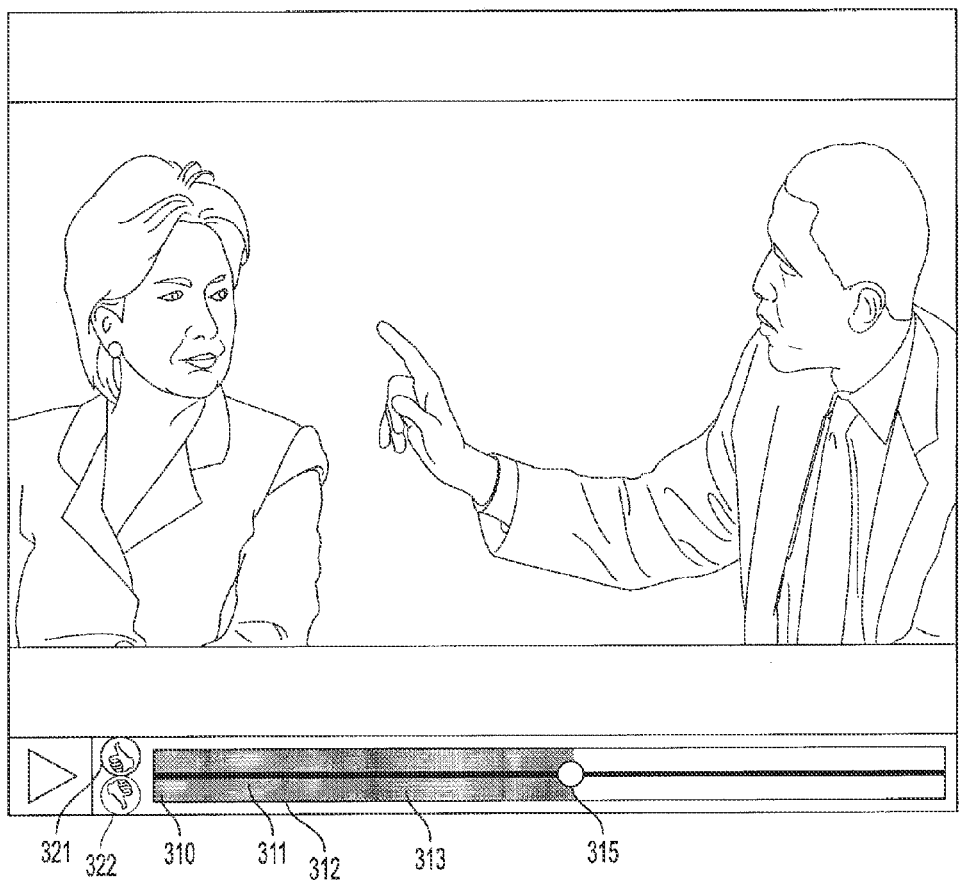

Referring again to FIG. 2, a video is displayed 210. The video server 126 of the video hosting website 108 retrieves data for the video from the video database 128 and provides it (e.g., via streaming) to the client 130, which then displays it, e.g. via the embedded player 134. Also displayed are controls for playback of the video, and also optionally for specifying voting data. For example, FIG. 3A illustrates one sample user interface for entering unipolar voting data. A video is displayed in video area 305, and an associated timeline 310 corresponds to the different segments of the video over time, with a marker 315 indicating the current position of the video being displayed. In general, the timeline 310 provides a representation of votes over time, using visual indications such as colors, bars, and the like positioned at locations along the timeline to illustrate the vote values. In FIG. 3A, the timeline 310 displays color gradients, such as gradient 325, to depict voting information from prior votes. The changes in color (depicted in black and white in FIG. 3A as shades of gray of greater or lesser intensity) show changes in voting across the different video segments, e.g. showing a change in total number of votes for each segment. The displayed prior votes may be only those of the viewer currently viewing and voting on the video, or they may include those historical votes previously submitted by other viewers before the viewer began to view the video (e.g. votes submitted in the previous 30 days, or some other set time frame), and/or they may include votes of other viewers who are watching the same video as the viewer, either synchronously (e.g., all viewers are watching a broadcast) or asynchronously (different viewers watching the video but starting at different times), or any combination of the foregoing (e.g., showing the aggregate of historical and current synchronous votes).

Referring back to FIG. 2, while the video is being displayed, voting data is received 220 at the client 130 from the user. (Such voting data may be in addition to voting data received at a previous time.) Voting can be done in real time while the video is being displayed, i.e. the user inputs a series of votes for a video on the client 130 substantially contemporaneously while the video is being played, so that the user's votes are received at substantially the same time that the user is making a judgment regarding the video content, rather than the user being obliged to halt playback of the video to vote, and/or to specify only a single vote representing an overall impression of the video content. Further, in one embodiment, each vote is received and stored at the video hosting website 108 substantially immediately after if it is entered at the client, including typical delays associated with transmissions over the network 105. Alternatively, the votes can be first cached at the client 130, and then transmitted in batch to the website 108, for example when the user finishes watching the video.

In FIG. 3A, for example, voting icon 320 may both provide a visual description of the types of votes associated with the video, and also serve as a means of entering votes. For example, the voting icon 320 indicates that the votes are unipolar (i.e., that there is only one type of vote, and that it is favorable, as illustrated with the thumbs-up image). Further, clicking on the voting icon 320 specifies a unipolar vote associated with a segment of the video corresponding to the marker 315 at the time the vote is input.

Votes can be submitted in a number of different manners in different embodiments. For example, a user could submit a vote using a graphical user interface provided by, for example, a web browser, such as clicking on voting icon 320 of FIG. 3A. Similarly, the user could click on a point on the timeline 310 to designate a unipolar vote for the segment of the video corresponding to the clicked point. Users may also click and drag on the timeline 310 to specify a unipolar vote for a longer interval of video, possibly comprising several distinct segments of the video. Users may also submit votes via a typical input device, such as a keyboard, where the press of a particular key corresponds to a given vote value. For example, a user could specify a unipolar vote by pressing any key, or a bipolar or categorical vote by pressing a key associated with an accepted value (e.g. "f" or "u", or "+" or "−", or up and down arrows for favorable or unfavorable values of a bipolar vote, or "b", "i", or "s" to designate "boring", "interesting", or "stimulating" in a categorical vote). The vote value is then associated with a time corresponding to the position of the marker 315.

After a user has submitted voting data, the client 130 then communicates the voting data to the vote storage module 144 of the video hosting website 108, which converts any raw values received into their corresponding semantic values and stores them in the vote database 142. A raw value is the data associated with input action, such as the value "f" of a keypress, and a semantic value describes the meaning associated with the raw value, such as a bipolar vote specifying a favorable value. Alternatively, the raw values can be converted to semantic values on the client 130 prior to being transmitted to the video hosting website 108.

Voting information specified by other users may or may not be displayed to the user at the time that the user is entering his or her own votes. Displaying votes of other users provides the user with a maximum of information, but runs the risk of introducing bias, leading the user to emulate the votes of the other users. If the potential for bias is a concern, the vote display module 118 can refrain altogether from displaying the data from other users in contexts when the user can vote, or it can display the voting data from other users only at times before the currently playing segment of the video. For example, the user interface of FIG. 3B displays only voting data in timeline 310 of other users associated with times prior to the current play time in the video, as indicated by video playback marker 315. The vote storage module 144 may additionally store whether or not a given vote was specified when the voting data of other users was available; such information could be used to optionally filter out possibly biased data when displaying voting data, or it could be analyzed to estimate the effects of bias on voting.

In one embodiment, the vote storage module 144 additionally associates a temporal indicator, such as a timestamp or a segment index, with the vote. This temporal indicator allows determining—directly or indirectly—the segment to which the vote corresponds. With regard to determining a segment index based on a timestamp, note that the timestamp corresponding to the time that the vote was specified on the client 130, or received by the video hosting website 108, need not correspond to the precise point in the video that prompted the user to submit the vote. For example, there will be some delay in the user's mental processes between the time at which the point of interest was played and when the user decides to vote on it, and some delay in the user's physical actions between the time that the user decides to vote on it and when he or she actually submits the vote, and these delays will vary among different users. However, as long as there is a large amount of vote data available, the vote storage module 144 can apply clustering algorithms to the votes, grouping votes nearby in time into a single common group, and then identifying a segment of the video associated with that group. For example, the vote storage module 144 could calculate an average vote time of the votes in the group, then adjust that time by subtracting a known estimate of the reaction time of the average user, e.g. 1 second. Each vote in the group is then associated with the segment containing that adjusted time, e.g. by associating the vote with the segment index of the segment.

The vote storage module 144 may also derive and store additional data in association with videos and/or segments of a given video. For example, the vote storage module 144 may compute a total number of votes for a particular segment of a video and store it in association with that segment, updating this stored total when additional votes are specified for that segment by additional users who watch the video and vote on that segment. Alternatively, the vote storage module 144 may compute a total value of the votes for a particular segment, rather than a raw count of the number of votes for that segment. For example, weights may be assigned to votes based on, for example, a reputation score of the user, the reputation score being based on factors such as whether the user is new or unrecognized, the usefulness of votes previously submitted by that user as rated by other users, or other information about the user within the user database 140.

Since multiple copies of a video may exist in the video database 128, each of which could receive separate voting data, voting data can become fragmented across different copies of the video, with some users viewing and voting on one particular copy, and other users viewing and voting on another copy. Thus, in one embodiment the vote storage module 144 additionally identifies any other copies of the same video that exist within the video database 128 and aggregates the voting data for the various copies of the video into a single set of data for that video. The vote storage module 144 can accomplish the identification of other copies of the video by a variety of means, such as by computing a similarity score between a set of representative feature vectors of each video. Each of the copies of the video is then associated with this aggregate vote data.

Figure 3C:
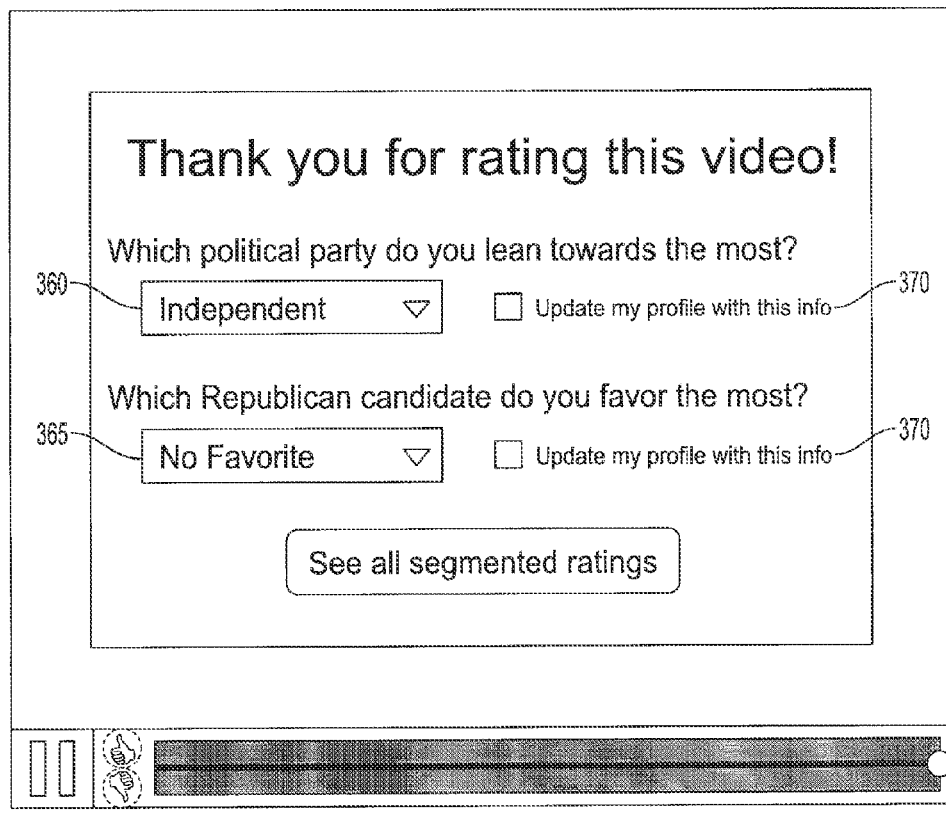

Each vote can also be associated with a set of demographic attributes, such as age, sex, political affiliation, and the like. In one embodiment, the demographic attributes are specified via a questionnaire provided along with the video, such as that depicted in FIG. 3C, which depicts a questionnaire related to a political video. In FIG. 3C, selection menu 360 allows the user to specify one of a set of political parties, and selection menu 365 allows the user to specify a particular candidate. Profile update checkboxes 370 allow the user to specify that the specified answers should be reflected in the user's profile on the video hosting website 108. Since the questionnaire is video-specific and can be created by the owner of the video, as well as by the video hosting website 108 itself, the questionnaire should include some data that specifies how the particular questions of the questionnaire correspond to the fields of the global profile of the video hosting website. Thus, the questionnaire may encode, for each field to be updated, an identifier that is standard for profiles on the video hosting website 108. For example, the update checkbox 370 for the political party selection menu 360 encodes an identifier specifying that the political party field of the user profile should be updated. Checkbox 370 may be omitted for questions not tied to a field of the user profile. The questionnaire could be part of the video itself, including interactive elements for specifying and providing input, or it could be a separate interactive multimedia unit that is linked to by the embedded video player 134 on the client 130 if the user provided any votes.

In another embodiment, the demographic attributes need not be explicitly specified by the user as in the interface of FIG. 3C, but can be automatically extracted from the profile of the user if the user has a profile that specifies values for the attributes in question. For example, if the user profile specifies a value of "Independent" for a "political party affiliation" attribute, then that value could be automatically set in selection menu 360 of FIG. 3C, for example, or the interface of FIG. 3C could alternatively be omitted entirely.

Regardless of the source of the attributes, the vote storage module 144 associates each vote received with respect to a video with the provided demographic attributes. For example, if the system-wide identity of the user—such as a user ID—is known, the votes can simply be associated with a system-wide entry for that user identity, the entry comprising the specified demographic attributes or the user ID for subsequent retrieval of the attributes. Alternatively, if no system-wide identity of the user is known, the votes by that user can still be grouped and stored in association with that particular video and with the specified demographic attributes.

Referring again back to FIG. 2, voting data is displayed 230. In FIG. 3A, for example, the timeline 310 may be graphically depicted to illustrate the voting data associated with the video, as is further described below; for example, the timeline of FIG. 3A contains color gradations indicating different numbers of votes for different segments.

The vote display module 118 provides for the display of an indication of previously stored voting data on a timeline associated with the videos. This provides a user with a visual summary of how users voted across the various segments of a video. The voting values can be displayed in different ways in different embodiments. For example, for unipolar votes, times corresponding to the different segments of the video can be colored differently, such as by associating a first color with a maximum vote value and a second color with a minimum vote value and computing a linear blend of the colors for a given segment of the video based on the vote value of that segment. For instance, a segment with no associated votes could be colored yellow, and a segment having a number (or value) of votes at or exceeding the maximum value could be colored red, and a segment with a vote value between those extremes could be colored an appropriate blend of yellow and red. This is depicted in grayscale form in the timeline 310 of FIG. 3A, where darker shades represent the color red, and lighter shades the color yellow.

In one embodiment, the display of the voting data, such as the timeline 310, is updated in real time as votes are entered. For example, the user's own votes for earlier segments of the video can be displayed substantially immediately after the votes are specified. Additionally, in some embodiments the votes of other users made at substantially the same time, e.g. after the user began to view the user interface 300 for the video, can be incorporated into the display. For example, the votes of other clients 130 for a given video can be stored in the vote database 142, and those votes, or updated graphical data reflecting those votes, can then be provided to each of the other clients 130 that is currently viewing that same video, and the display of the clients can be updated accordingly.

Figure 3D:
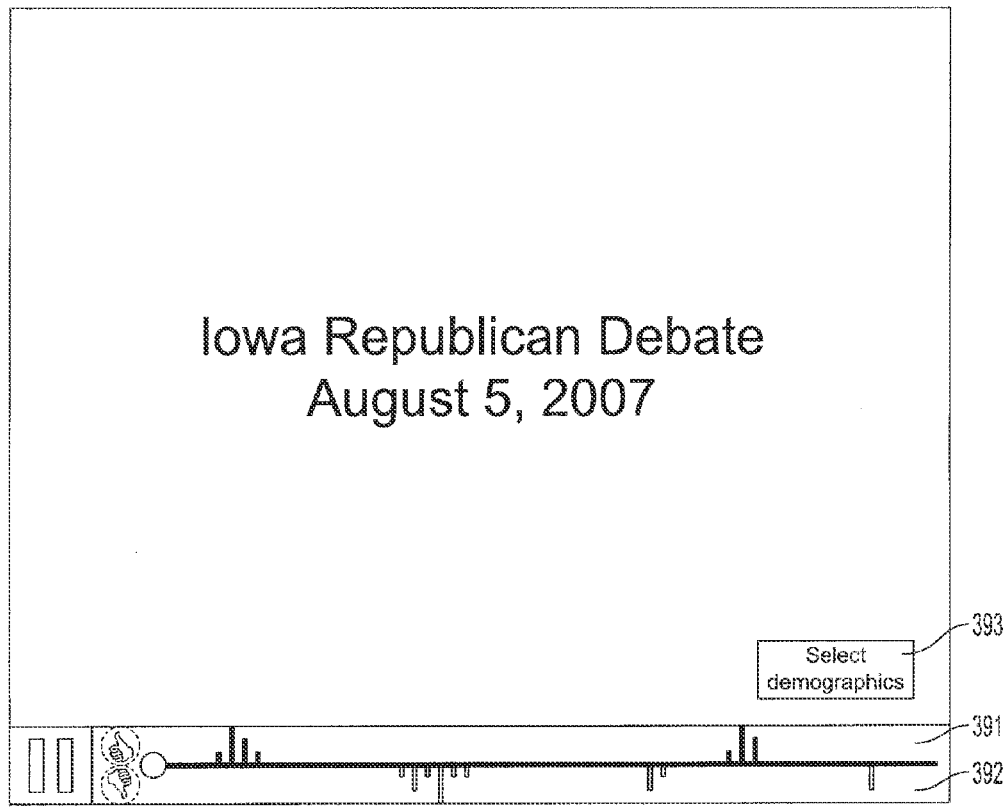

In the case of bipolar voting, such as favorable versus unfavorable votes, each can be assigned a color and the net value computed for a given segment of the video. For example, referring back to FIG. 3B, color gradients 311-313 are indicated on the timeline 310 corresponding to segments where the voting is largely favorable, largely unfavorable, and a roughly equal, respectively. Although represented in grayscale in FIG. 3B, the colors for the gradients 311-313 represent the color associated with favorable icon 321, the color associated with the unfavorable icon 322, and a blend thereof, respectively. The color of a particular color gradient can be a linear blend of the colors representing the number of favorable and unfavorable votes. For example, if favorable votes are represented by the color red, and unfavorable votes by the color blue, then a segment with 60% favorable votes and 40% unfavorable votes could be represented with a linear blend having 60% red and 40% blue, resulting in a shade of purple. Alternatively, the overall color could be that corresponding to the majority of the votes, and the saturation of the color could be based on how strong the majority is. For example, for a segment of the video for which there are 150 red (favorable) votes and 100 blue (unfavorable) votes, the segment could be colored red, with the 50-vote difference between the total of 250 favorable and unfavorable votes used to determine the intensity of the red. As an alternative example, votes can be represented with a graph, such as the bar charts depicted in FIG. 3D, which comprises one bar chart area 391 representing favorable votes over time, and another bar chart area 392 representing unfavorable votes over time, with longer bars representing more votes for the corresponding segments, and the horizontal position of each bar corresponding to the approximate time of the votes contributing to the bar. FIG. 3D also depicts a button 393 for the selection of particular demographics, e.g., filtering the voting data to show just that voting data associated with users of a particular political party.

Figure 3E:
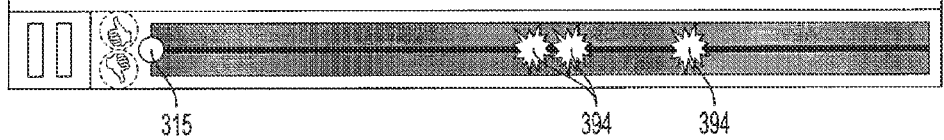

In general, there can be video segments for which there are strong differences of opinion among the users viewing the video, such as a large number of both favorable and unfavorable votes for the same segment in the case of bipolar voting; this could indicate an area of controversy or dispute. For example, this might occur in the context of a video of a political debate, with Democratic viewers voting strongly in favor of a particular segment of the video (e.g., in which a Democratic candidate made a statement appealing to Democratic viewers), and Republican viewers voting strongly against it. In general, controversies are detected by quantifying a level of divergence among the votes for the segment and comparing the quantified divergence to a threshold value. In one embodiment for bipolar voting, such "controversial" segments are detected by computing the ratio of favorable to unfavorable votes, and determining the distance of this ratio from 0.5 (indicating split votes), with distances less than some specified threshold distance (e.g., 0.1) indicating a controversy. In other embodiments, it is additionally preliminarily determined whether there is a sufficient total number of votes (e.g., 100 votes); if not, then it is not deemed important enough to represent a controversy. Such controversies can be difficult to visually detect for some types of visual display, such as color blending, where an equal number of positive and negative values produces the same blended color, regardless of whether votes are unanimously neutral or strongly but equally divided. Thus, in some embodiments the system can additionally provide a visual indicator to clearly identify such segments of controversy. For example, FIG. 3E depicts three star-shaped controversy indicators 394 corresponding to three segments in which there are a large number of both positive and negative votes. Users can then move playback to those controversial segments of the video, e.g. by clicking at those locations or dragging the marker 315 to them.

Figure 3F:
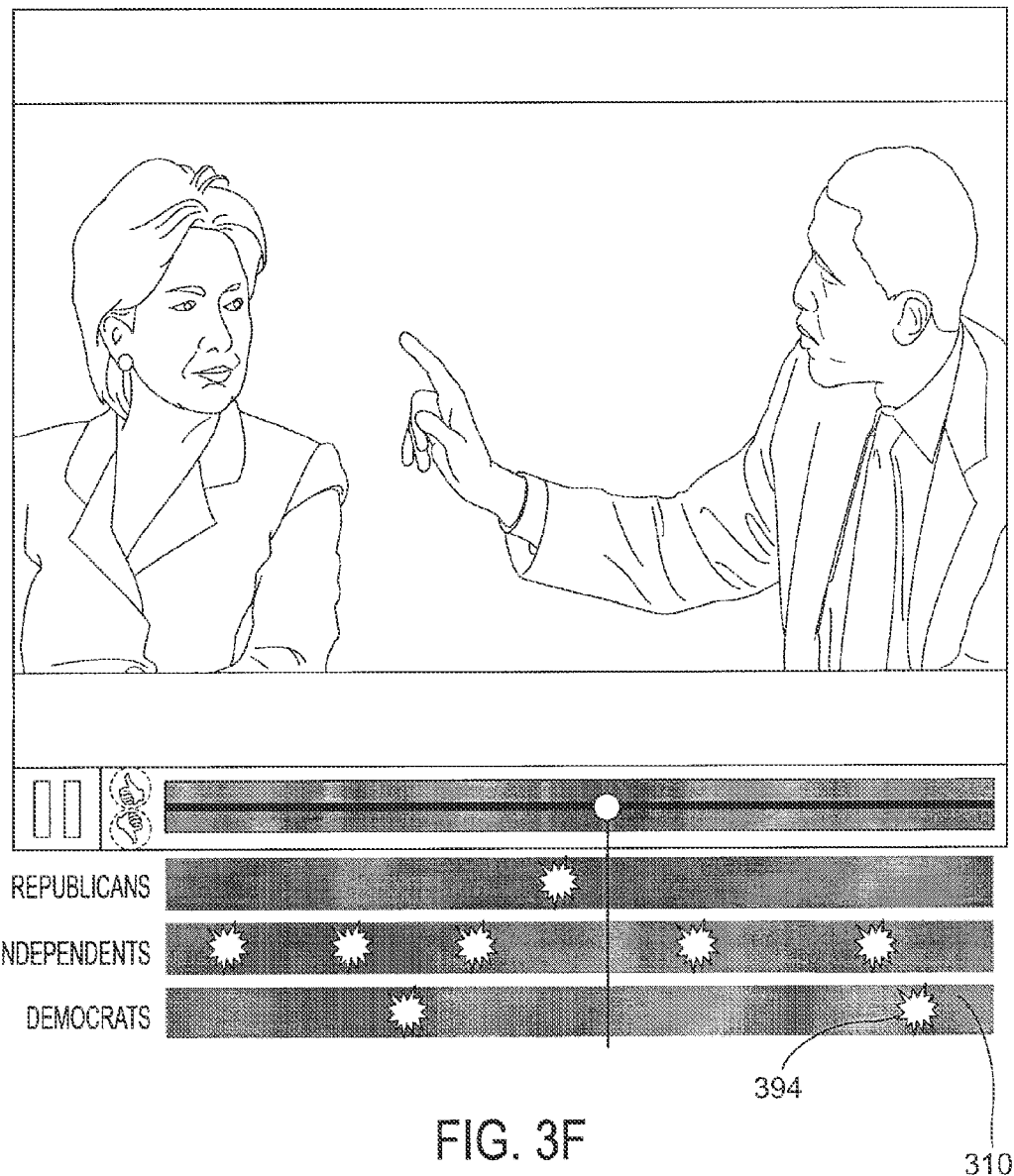

Controversies may be shown between different demographic groups, e.g. all voters, as in FIG. 3E, or within a single group. For example, FIG. 3F illustrates showing separate voting data and separate controversy indicators 394 on separate timelines 310 for each, e.g. within the Republican, Independent, and Democratic groups.

Figure 3G:
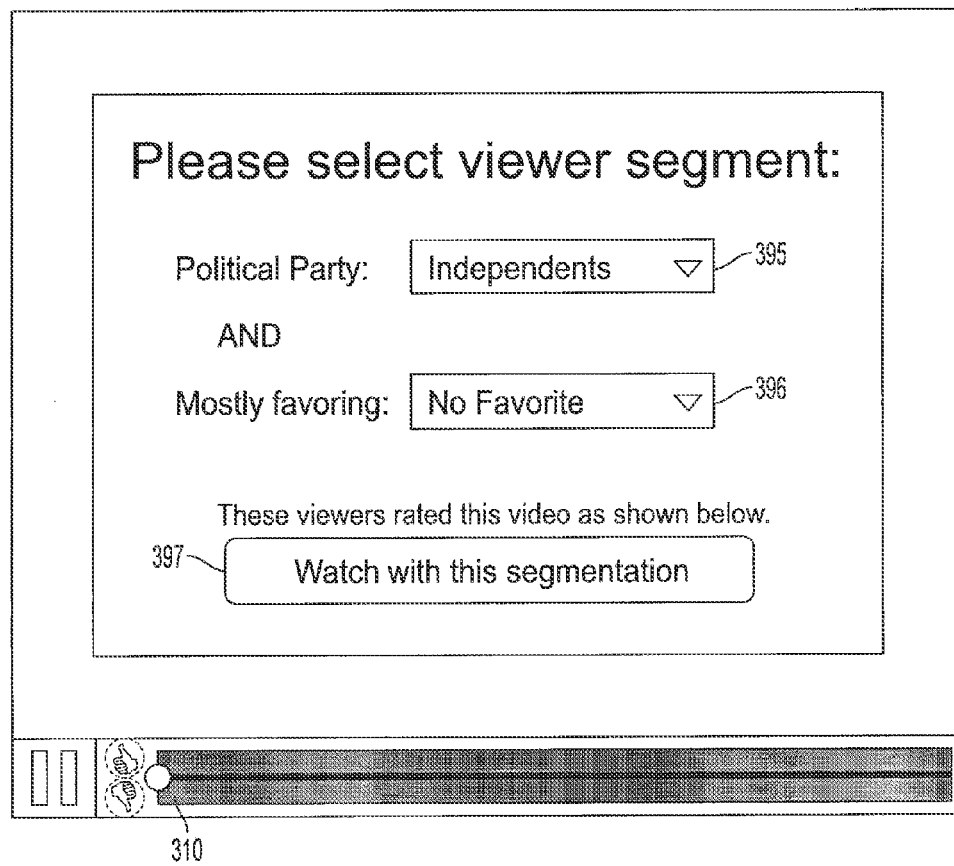

The previously stored voting data can also be filtered and used to focus on segments of interest within the video. For example, FIG. 3G depicts a user interface for specifying watching a video segmented according to a given demographic attribute or attributes, e.g., political party. Specifically, FIG. 3G shows selection lists 395 and 396 for selecting votes by those of a particular party, and who mostly favor a particular candidate, respectively. In response to, for instance, selection of button 397, the selected attribute values are then applied as filters, selecting only votes associated with the selected demographic attribute values. The identified votes are then displayed on the timeline 310, e.g., as a group visually distinct from votes not associated with the selected demographic attribute values. For example, only the votes associated with the selected demographic attribute values may be displayed, or they may be displayed in addition to but separately from other votes, such as on a separate timeline, as in FIG. 3F, where each value of the political party demographic attribute (e.g., Republicans, Independents, Democrats) is depicted on a separate timeline.

Additionally, the client player 134 can be set to play only those segments of the video that are considered of interest to the selected demographics, e.g. those segments having particularly high voting values, or segments that are determined to be controversial. The user interface of FIG. 3G could be shown at different times in different embodiments, such as at the start of the video, at the end of the video, or in response to a user request to select segments of interest to given demographics, e.g. via selection of the button 393 of FIG. 3D. In one embodiment, the client 130 transmits a designation of the selected demographic categories to the video hosting website 108, which then determines which segments of the video have at least a threshold number of votes that are associated with a demographic attribute value(s) matching the designated demographic attribute value(s), and then provides an indication of the determined segments (e.g., a segment identifier) to the client 130, which can then display only those segments. For example, if a viewer selected "Independent" as a political party demographic attribute value, then the video hosting website 108 would provide to the client 130 an indication of only the segments with at least a threshold number of votes associated with the Independent political party, e.g. those votes by viewers with profiles specifying that party.

Reference in the specification to "one embodiment" or to "an embodiment" means that a particular feature, structure, or characteristic described in connection with the embodiments is included in at least one embodiment of the invention. The appearances of the phrase "in one embodiment" in various places in the specification are not necessarily all referring to the same embodiment.

It should be noted that the process steps and instructions of the present invention can be embodied in software, firmware or hardware, and when embodied in software, can be downloaded to reside on and be operated from different platforms used by a variety of operating systems.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and displays presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein, and any references below to specific languages are provided for disclosure of enablement and best mode of the present invention.

While the invention has been particularly shown and described with reference to a preferred embodiment and several alternate embodiments, it will be understood by persons skilled in the relevant art that various changes in form and details can be made therein without departing from the spirit and scope of the invention.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention, which is set forth in the following claims.

What is claimed is:

1. A computer-implemented method of associating a series of votes with a video, the method comprising:
transmitting the video for display to a client device of a viewer;
receiving a first series of votes from the viewer, each vote having a vote value;
storing the first series of votes in a storage medium;
receiving a second series of votes of other viewers;
associating votes of the first series of votes and of the second series of votes with demographic attribute values;
selecting one of the demographic attribute values;
identifying, from at least one of the first series of votes and the second series of votes, votes associated with the selected demographic attribute value; and
providing, to the client device for display, a graphical timeline representation comprising the vote values of the first series of votes and vote values of the second series of votes, wherein the votes associated with the selected demographic attribute value are represented on the graphical timeline representation as a group visually distinct from votes not associated with the selected demographic attribute value.

2. The computer-implemented method of claim 1, wherein the video has a plurality of segments, wherein the votes of the first series of votes and of the second series of votes are associated with ones of the segments, and wherein providing the graphical timeline representation further comprises:
identifying a controversial video segment by quantifying a level of divergence among the votes associated with the segment and comparing the quantified level of divergence to a threshold; and
providing to the client device, for display on the provided graphical timeline representation at a location associated in time with the controversial video segment, a visual indicator of the controversy.

3. The computer-implemented method of claim 1, wherein the graphical timeline representation displays the vote values as gradations of color.

4. The computer-implemented method of claim 1, wherein the graphical timeline representation displays the vote values as a graph.

5. The computer-implemented method of claim 1, wherein the second series of votes includes votes from other viewers watching the video synchronously with the viewer.

6. The computer-implemented method of claim 1, wherein the second series of votes includes votes from other viewers watching the video asynchronously with the viewer.

7. The computer-implemented method of claim 1, wherein the second series of votes includes historical votes from other viewers having watched the video before the viewer began to view the video.

8. The computer-implemented method of claim 1, wherein the video has a plurality of segments, and wherein the votes of the first series of votes and of the second series of votes are associated with ones of the segments, the method further comprising:
responsive at least in part to receiving from the viewer a designation of a value of a demographic attribute:
determining segments of the video having at least a threshold number of votes that are associated with a demographic attribute value matching the designated demographic attribute value; and
providing, to a client device of the viewer, an indication of the determined segments of the video.

9. A non-transitory computer-readable storage medium storing a computer program executable by a computer system for voting on a digital video, the computer program controlling the computer system to perform operations comprising:
receiving the video;
receiving, from the viewer, a series of votes, each vote having a vote value;
selecting a demographic attribute value;
receiving from a vote database a second series of votes, the second series of votes being associated with the selected demographic attribute value; and
displaying a graphical timeline representation of the received votes and of the second series of votes, wherein the graphical timeline representation displays the second series of votes as a group visually distinct from votes not associated with the selected demographic attribute value.

10. The computer-readable storage medium of claim 9, wherein the vote value is selected by the viewer from a multipolar set of potential values.

11. The computer-readable storage medium of claim 9, wherein the video has a plurality of segments and wherein the votes of the first series of votes and of the second series of votes are associated with ones of the segments, the operations of the computer program further comprising:
receiving an indication of a video segment having a quantified level of divergence among the votes associated with the segment greater than a specified threshold; and
displaying an indicator of a controversy at a location on the graphical timeline representation corresponding to the video segment for which the indication was received.

12. The computer-readable storage medium of claim 9, wherein the graphical timeline representation displays the vote values as gradations of color.

13. The computer-readable storage medium of claim 9, wherein the graphical timeline representation displays the vote values as a graph.

14. The computer-readable storage medium of claim 9, wherein the video has a plurality of segments, and wherein the votes of the first series of votes and of the second series of votes are associated with ones of the segments, the operations of the computer program further comprising:
receiving from the viewer a designation of a value of a demographic attribute;
responsive at least in part to the receiving of the designation, displaying, within the video playback area, segments of the video having at least a threshold number of votes that are associated with a demographic attribute value matching the designated demographic attribute value.

15. A computer system for associating a series of votes with a first video, the system comprising:
a video database storing a plurality of videos including the first video;
a vote database storing votes associated with videos;
a module configured to perform operations comprising:
transmitting the first video from the video database for display to a client device of a viewer;
receiving a first series of votes from the viewer, each vote having a vote value, the vote value selected by the viewer from a multipolar set of potential values;
storing the first series of votes in the vote database in association with information identifying the first video;
receiving a second series of votes of other viewers;
associating votes of the first series of votes and of the second series of votes with demographic attribute values;
selecting one of the demographic attribute values;
identifying, from at least one of the first and second series of votes, votes associated with the selected demographic attribute value; and
providing, to the client device for display, a graphical timeline representation comprising the vote values of the first series of votes and vote values of the second series of votes, wherein the votes associated with the selected demographic attribute value are represented on the graphical timeline representation as a group visually distinct from votes not associated with the selected demographic attribute value.

16. The computer system of claim 15, wherein the video has a plurality of segments, wherein the votes of the first series of votes and of the second series of votes are associated with ones of the segments, and wherein providing the graphical timeline representation further comprises:
identifying a video segment by quantifying a level of divergence among the votes associated with the segment and comparing the quantified level of divergence to a threshold; and
providing to the client device, for display on the provided graphical timeline representation at a location associated in time with the identified video segment, a visual indicator of a controversy.

17. The computer system of claim 15, wherein the graphical timeline representation displays the vote values as gradations of color.

18. The computer system of claim 15, wherein the graphical timeline representation displays the vote values as a graph.

19. The computer system of claim 15, the actions of the module further comprising:

responsive at least in part to receiving from the viewer a designation of one of the demographic attribute values:
  determining segments of the video having at least a threshold number of votes that are associated with a demographic attribute value matching the designated demographic attribute value; and
  providing, to a client device of the viewer, an indication of the determined segments of the video.

20. A computer-implemented method of displaying voting information for a video, the video viewed by a plurality of viewers on a plurality of respective client devices, the video having a plurality of segments, the method comprising:
  transmitting the video to the plurality of client devices of the plurality of viewers, whereby the video is displayed on the client devices;
  receiving from each viewer's client device, while the video is being displayed on that viewer's client device, a series of votes from the viewer, each vote associated with a segment of the video and having a vote value;
  for each segment of the video, aggregating the received votes associated with that segment, according to the vote values, to form aggregated voting information; and
  providing, for display to at least one of the plurality of client devices, a graphical timeline representation comprising the vote values of the series of votes and vote values of a second series of votes received from other viewers, the providing comprising:
    associating votes of the first and second series of votes with demographic attribute values;
    responsive to receiving a selection of one of the demographic attribute values:
      identifying, from the first and second series of votes, votes associated with the selected demographic attribute value; and
      providing, to the client device for display, a representation of the identified votes on the graphical timeline representation as a group visually distinct from votes not associated with the selected demographic attribute value.

21. The computer-implemented method of claim 20, further comprising transmitting the aggregated voting information to a plurality of client devices for display thereon concurrently with display of the video.

22. A computer-implemented method of displaying voting information for a video, the video comprising a plurality of segments, each segment associated with aggregated voting information for votes specified by viewers, the votes having values selected by the viewers from a multipolar set of potential values, the votes being associated with demographic attribute values, the aggregated voting information comprising a total number of votes for each potential value of the multipolar set, the method comprising:
  transmitting the video to a client device of a viewer, whereby the segments of the video are displayed on the client device; and
  transmitting for display on the client device concurrently with display of the video, the aggregated voting information for previously displayed segments of the video;
  responsive to receiving a selection of one of the demographic attribute values, identifying votes associated with the selected demographic attribute value; and
  transmitting, to the client device for display, a graphical timeline representation comprising the vote values of the votes, wherein the votes associated with the selected demographic attribute value are represented on the graphical timeline representation as a group visually distinct from votes not associated with the selected demographic attribute value.

* * * * *